US009784635B2

United States Patent
Bizub

(10) Patent No.: US 9,784,635 B2
(45) Date of Patent: Oct. 10, 2017

(54) SYSTEMS AND METHODS FOR DETECTION OF ENGINE COMPONENT CONDITIONS VIA EXTERNAL SENSORS

(71) Applicant: General Electric Company, Schenectady, NY (US)

(72) Inventor: Jeffrey Jacob Bizub, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 284 days.

(21) Appl. No.: 14/754,128

(22) Filed: Jun. 29, 2015

(65) Prior Publication Data

US 2016/0377500 A1 Dec. 29, 2016

(51) Int. Cl.
| | |
|---|---|
| *G01L 23/22* | (2006.01) |
| *F02D 41/14* | (2006.01) |
| *F02D 41/22* | (2006.01) |
| *F02D 35/02* | (2006.01) |
| *G01M 15/05* | (2006.01) |
| *G01M 15/12* | (2006.01) |

(Continued)

(52) U.S. Cl.
CPC .......... *G01L 23/221* (2013.01); *F02D 35/027* (2013.01); *F02D 41/1497* (2013.01); *F02D 41/22* (2013.01); *G01M 15/05* (2013.01); *G01M 15/12* (2013.01); *G01N 29/14* (2013.01); *G01N 29/449* (2013.01); *F02D 2200/025* (2013.01)

(58) Field of Classification Search
CPC .. F02D 41/22; F02D 41/1497; F02D 41/1498; F02D 35/027; G01L 23/22; G01L 23/221; F02B 77/085; F02B 77/089

USPC ........... 123/406.24, 406.26, 406.34, 406.37, 123/406.4, 435–436; 73/114.01, 114.02, 73/114.07; 701/111, 115
See application file for complete search history.

(56) References Cited

U.S. PATENT DOCUMENTS

| 4,373,396 A * | 2/1983 | Johnson ................ G01L 9/0022 73/35.11 |
| 5,029,565 A | 7/1991 | Talbot |

(Continued)

FOREIGN PATENT DOCUMENTS

| CN | 203480037 | 3/2014 |
| EP | 1447654 | 8/2004 |

(Continued)

OTHER PUBLICATIONS

U.S. Appl. No. 14/790,785, filed Jul. 2, 2015, Pavan Chakravarthy Nandigama.

(Continued)

*Primary Examiner* — Thomas Moulis
(74) *Attorney, Agent, or Firm* — Fletcher Yoder, P.C.

(57) ABSTRACT

In one embodiment, a method is provided. The method includes receiving a plurality of signals representative of an engine noise transmitted via a plurality of noise sensors, wherein the noise sensors are disposed in a grid about an engine. The method further includes receiving a knock sensor signal representative of an engine noise transmitted via a knock sensor. The method additionally includes deriving a combustion event based on the knock sensor signal, and deriving an engine condition based on the plurality of signals and the combustion event. The method also includes communicating the engine condition.

20 Claims, 5 Drawing Sheets

(51) Int. Cl.
*G01N 29/14* (2006.01)
*G01N 29/44* (2006.01)

(56) References Cited

U.S. PATENT DOCUMENTS

| | | | |
|---|---|---|---|
| 5,080,065 A * | 1/1992 | Nomura | F02B 29/083 |
| | | | 123/184.54 |
| 5,111,790 A | 5/1992 | Grandy | |
| 5,115,778 A | 5/1992 | Holroyd | |
| 5,119,783 A | 6/1992 | Komurasski | |
| 5,241,480 A | 8/1993 | Takaku et al. | |
| 5,257,533 A | 11/1993 | Imada | |
| 5,287,837 A * | 2/1994 | Hashimoto | F02P 5/152 |
| | | | 123/406.29 |
| 5,337,240 A | 8/1994 | Nakagawa et al. | |
| 5,339,245 A | 8/1994 | Hirata et al. | |
| 5,361,213 A | 11/1994 | Fujieda et al. | |
| 5,386,367 A * | 1/1995 | Ziegler | F02P 5/1522 |
| | | | 123/435 |
| 5,392,642 A | 2/1995 | Tao | |
| 5,400,648 A | 3/1995 | Mahr | |
| 5,428,986 A * | 7/1995 | Dietsche | G01L 23/225 |
| | | | 73/35.04 |
| 5,447,136 A * | 9/1995 | Hartmann | F02P 3/0456 |
| | | | 123/625 |
| 5,452,699 A | 9/1995 | Rossignol | |
| 5,467,638 A | 11/1995 | Philipp | |
| 5,594,649 A * | 1/1997 | Cook | G01L 23/225 |
| | | | 123/406.37 |
| 5,693,936 A | 12/1997 | Komachiya et al. | |
| 5,739,417 A * | 4/1998 | Grob | F02D 35/027 |
| | | | 73/114.07 |
| 5,763,769 A | 6/1998 | Kluzner | |
| 5,837,887 A | 11/1998 | Shibata et al. | |
| 5,905,193 A | 5/1999 | Hashizume et al. | |
| 5,932,801 A | 8/1999 | Akishita et al. | |
| 5,934,256 A * | 8/1999 | Wenzlawski | F02D 41/1497 |
| | | | 123/406.14 |
| 5,945,596 A * | 8/1999 | Burkel | F02D 41/1497 |
| | | | 73/114.38 |
| 5,996,398 A | 12/1999 | Schleupen et al. | |
| 6,012,425 A * | 1/2000 | Unland | G01L 23/225 |
| | | | 123/406.38 |
| 6,062,199 A * | 5/2000 | Entenmann | F02P 5/1522 |
| | | | 123/406.21 |
| 6,104,195 A | 8/2000 | Yoshinaga et al. | |
| 6,246,953 B1 * | 6/2001 | Quinn | F02D 35/027 |
| | | | 123/406.34 |
| 6,273,064 B1 | 8/2001 | Scholl et al. | |
| 6,276,334 B1 | 8/2001 | Flynn et al. | |
| 6,330,877 B1 | 12/2001 | Nordin | |
| 6,336,355 B1 | 1/2002 | Sasaki et al. | |
| 6,550,311 B2 | 4/2003 | Sloboda | |
| 6,591,660 B1 * | 7/2003 | Franke | F02D 35/027 |
| | | | 73/35.03 |
| 6,598,468 B2 | 7/2003 | Zur Loye et al. | |
| 6,662,781 B1 | 12/2003 | Torno et al. | |
| 6,727,812 B2 * | 4/2004 | Sauler | F02D 41/222 |
| | | | 123/406.16 |
| 6,741,919 B1 * | 5/2004 | Schuster | G05B 9/02 |
| | | | 701/29.4 |
| 6,814,054 B2 | 11/2004 | Sauler et al. | |
| 6,862,517 B2 | 3/2005 | Galtier | |
| 6,885,932 B2 | 4/2005 | Liu et al. | |
| 6,912,460 B2 | 6/2005 | Sauler et al. | |
| 6,947,829 B2 | 9/2005 | Honda | |
| 6,978,771 B2 | 12/2005 | Kuzuyama et al. | |
| 6,990,947 B2 | 1/2006 | Kuzuyama et al. | |
| 7,021,128 B2 | 4/2006 | Rauchfuss et al. | |
| 7,027,909 B2 | 4/2006 | deBotton et al. | |
| 7,103,460 B1 | 9/2006 | Breed | |
| 7,181,338 B2 | 2/2007 | Takemura et al. | |
| 7,191,658 B2 | 3/2007 | Oda et al. | |
| 7,212,909 B2 | 5/2007 | Yoshino et al. | |
| 7,231,289 B2 * | 6/2007 | Damitz | F02D 35/02 |
| | | | 123/435 |
| 7,243,529 B2 | 7/2007 | Takemura et al. | |
| 7,246,600 B2 | 7/2007 | Nakashima et al. | |
| 7,260,469 B2 | 8/2007 | Birk et al. | |
| 7,263,872 B2 | 9/2007 | Danet et al. | |
| 7,310,993 B2 | 12/2007 | Popielas et al. | |
| 7,325,529 B2 | 2/2008 | Ancimer et al. | |
| 7,356,404 B2 | 4/2008 | Takemura et al. | |
| 7,376,506 B2 | 5/2008 | Schueler | |
| 7,383,816 B2 | 6/2008 | Zurlo | |
| 7,444,231 B2 | 10/2008 | Ancimer et al. | |
| 7,444,236 B2 | 10/2008 | Wiles | |
| 7,448,254 B2 | 11/2008 | Kurtz et al. | |
| 7,546,198 B2 * | 6/2009 | Remelman | F02D 35/027 |
| | | | 123/406.21 |
| 7,559,230 B2 | 7/2009 | Zimmer | |
| 7,571,640 B2 | 8/2009 | Andrews | |
| 7,628,253 B2 | 12/2009 | Jin et al. | |
| 7,669,582 B2 | 3/2010 | Kaneko et al. | |
| 7,712,450 B2 | 5/2010 | Sato et al. | |
| 7,747,380 B2 | 6/2010 | Chauvin et al. | |
| 7,810,469 B2 | 10/2010 | Vigild et al. | |
| 7,823,561 B2 | 11/2010 | Omuro et al. | |
| 7,881,855 B2 * | 2/2011 | Damitz | F02D 35/02 |
| | | | 123/299 |
| 7,957,892 B2 * | 6/2011 | Hyde | F01N 9/00 |
| | | | 60/274 |
| 8,000,884 B2 | 8/2011 | Aso et al. | |
| 8,032,293 B2 | 10/2011 | Binder et al. | |
| 8,068,972 B2 | 11/2011 | Auclair et al. | |
| 8,078,389 B2 | 12/2011 | Huang et al. | |
| 8,079,261 B2 | 12/2011 | Crickmore et al. | |
| 8,108,131 B2 | 1/2012 | Huang et al. | |
| 8,155,857 B2 * | 4/2012 | Loeffler | F02D 35/023 |
| | | | 123/435 |
| 8,229,624 B2 | 7/2012 | Breed | |
| 8,250,905 B2 | 8/2012 | Schneider et al. | |
| 8,260,531 B2 | 9/2012 | Yasuda | |
| 8,316,824 B2 | 11/2012 | Hagari et al. | |
| 8,342,011 B2 | 1/2013 | Galtier et al. | |
| 8,359,909 B2 | 1/2013 | Duval et al. | |
| 8,396,649 B2 | 3/2013 | Huang | |
| 8,463,533 B2 | 6/2013 | Glugla et al. | |
| 8,499,623 B2 | 8/2013 | Duval et al. | |
| 8,528,521 B2 | 9/2013 | Landsmann et al. | |
| 8,538,666 B2 | 9/2013 | Buslepp et al. | |
| 8,584,515 B2 * | 11/2013 | Fischer | F02M 51/061 |
| | | | 73/114.45 |
| 8,606,484 B2 | 12/2013 | Ohata | |
| 8,627,800 B2 | 1/2014 | Glugla et al. | |
| 8,639,432 B2 | 1/2014 | Matsuo et al. | |
| 8,655,571 B2 * | 2/2014 | Geib | F01D 21/003 |
| | | | 701/100 |
| 8,677,975 B2 | 3/2014 | Auclair et al. | |
| 8,680,707 B2 | 3/2014 | Childs et al. | |
| 8,849,471 B2 | 9/2014 | Daniel et al. | |
| 2004/0003651 A1 * | 1/2004 | Rauchfuss | G01L 23/225 |
| | | | 73/35.07 |
| 2005/0216175 A1 * | 9/2005 | Takahashi | F02D 41/1454 |
| | | | 701/109 |
| 2007/0033997 A1 * | 2/2007 | Schueler | F02B 77/085 |
| | | | 73/117.03 |
| 2007/0050124 A1 * | 3/2007 | Birk | F02D 35/023 |
| | | | 701/111 |
| 2007/0255563 A1 | 11/2007 | Dooley | |
| 2008/0134789 A1 | 6/2008 | Schneider et al. | |
| 2009/0112449 A1 * | 4/2009 | Binder | F02D 35/02 |
| | | | 701/111 |
| 2009/0118989 A1 * | 5/2009 | Padhi | G01L 23/225 |
| | | | 701/111 |
| 2009/0177354 A1 | 7/2009 | Agrawal et al. | |
| 2010/0011849 A1 * | 1/2010 | Robinson | F02D 33/003 |
| | | | 73/114.43 |
| 2010/0018500 A1 * | 1/2010 | Itano | F02P 5/152 |
| | | | 123/406.38 |
| 2010/0300683 A1 * | 12/2010 | Looper | E21B 47/0007 |
| | | | 166/250.01 |

(56) References Cited

U.S. PATENT DOCUMENTS

| | | | | |
|---|---|---|---|---|
| 2011/0093182 A1* | 4/2011 | Weber | ............... | F02D 41/0007 701/102 |
| 2012/0285161 A1* | 11/2012 | Kerns | ............... | F02D 41/0087 60/598 |
| 2012/0330575 A1 | 12/2012 | Weber et al. | | |
| 2013/0166184 A1* | 6/2013 | Wuerth | ............... | F02D 35/02 701/111 |
| 2014/0172279 A1* | 6/2014 | Qiao | ............... | F02D 41/1498 701/111 |
| 2014/0172280 A1* | 6/2014 | Ogata | ............... | G01H 17/00 701/111 |
| 2015/0006066 A1* | 1/2015 | Stevens | ............... | F02D 41/2451 701/115 |
| 2016/0370254 A1* | 12/2016 | Rivellini | ............... | G01M 15/05 |

FOREIGN PATENT DOCUMENTS

| | | |
|---|---|---|
| EP | 1698775 | 6/2006 |
| EP | 1840360 | 3/2007 |
| EP | 1988378 | 5/2008 |
| EP | 2128409 | 2/2009 |
| EP | 2128410 | 2/2009 |
| EP | 2433355 | 3/2012 |
| EP | 2500705 | 9/2012 |
| EP | 3040544 A1 | 7/2016 |
| JP | 2002107223 A | 4/2002 |
| JP | 2011256833 A | 12/2011 |
| WO | WO2008000568 | 1/2008 |
| WO | WO2008059376 | 5/2008 |
| WO | WO 2009106557 | 9/2009 |
| WO | WO2013015372 | 1/2013 |
| WO | WO2013026950 | 2/2013 |
| WO | WO 2013118151 | 8/2013 |
| WO | 2014168937 A2 | 10/2014 |

OTHER PUBLICATIONS

U.S. Appl. No. 14/796,934, filed Jul. 10, 2015, Jeffrey Jacob Bizub.
U.S. Appl. No. 14/820,156, filed Aug. 6, 2015, Jeffrey Jacob Bizub.
U.S. Appl. No. 14/918,013, filed Oct. 20, 2015, Venkatesh Raman.
U.S. Appl. No. 14/320,101, filed Jun. 30, 2014, Ryan Thomas Smith.
U.S. Appl. No. 14/587,407, filed Dec. 31, 2014, Jeffrey Jacob Bizub.
U.S. Appl. No. 14/587,412, filed Dec. 31, 2014, Jerry Jacob Bizub.
U.S. Appl. No. 14/587,434, filed Dec. 31, 2014, Jeffrey Jacob Bizub.
U.S. Appl. No. 14/591,192, filed Jan. 7, 2015, Jeffrey Jacob Bizub.
U.S. Appl. No. 14/592,547, filed Jan. 8, 2015, Jeffrey Jacob Bizub.
U.S. Appl. No. 14/600,674, filed Jan. 20, 2015, Scott K. Mann.
U.S. Appl. No. 14/609,416, filed Jan. 29, 2015, Jeffrey Jacob Bizub.
U.S. Appl. No. 14/614,237, filed Feb. 4, 2015, Pin Zeng.
U.S. Appl. No. 14/617,458, filed Feb. 9, 2015, Jeffrey Jacob Bizub.
U.S. Appl. No. 14/621,028, filed Feb. 15, 2015, Jeffrey Jacob Bizub.
U.S. Appl. No. 14/626,385, filed Feb. 19, 2015, Jeffrey Jacob Bizub.
U.S. Appl. No. 14/639,736, filed Mar. 5, 2015, Jeffrey Jacob Bizub.
U.S. Appl. No. 14/644,526, filed Mar. 11, 2015, Jeffrey Jacob Bizub.
U.S. Appl. No. 14/657,817, filed Mar. 13, 2015, Jeffrey Jacob Bizub.
U.S. Appl. No. 14/676,733, filed Apr. 1, 2015, Jeffrey Jacob Bizub.
U.S. Appl. No. 14/686,350, filed Apr. 14, 2015, Maruthi Narasinga Rao Devarakonda.
U.S. Appl. No. 14/695,335, filed Apr. 24, 2015, Jeffrey Jacob Bizub.
U.S. Appl. No. 14/705,081, filed May 6, 2015, Scott K. Mann.
U.S. Appl. No. 14/745,986, filed Jun. 22, 2015, Sandro Rivellini.
Reduction Piston Slap Excitation by Optimizing Piston Profiles; Takayuki Koizumi et al.; Proc. of 2002 IMAC-XX: Conf. & Exposition on Structural Dynamics, Jun. 12-15, 2000.
VE Piston Dynamics; FEV Group, Inc.; available online; www.fev.com/what-we-do/software/virtual-engine-powertrain-dynamics-simulation/piston-dynamics-module; Jan. 1, 2015.
Diagnostic Internal Combustion Engine Based on Crankshaft Angular Acceleration; Binh Le Khac, Tuma J.; available online; www.researchgate.net, May 2012.
Bolt loosening detection using vibration characteristics of thin plate with piezoelectric elements;Takeshi Nakahara et al; Proc.of SPIE 5391, Smart Struc. & Materials, Jul. 2004.
International Search Report and Written Opinion issued in connection with corresponding PCT Application No. PCT/US2016/039153 on Oct. 14, 2016.

\* cited by examiner

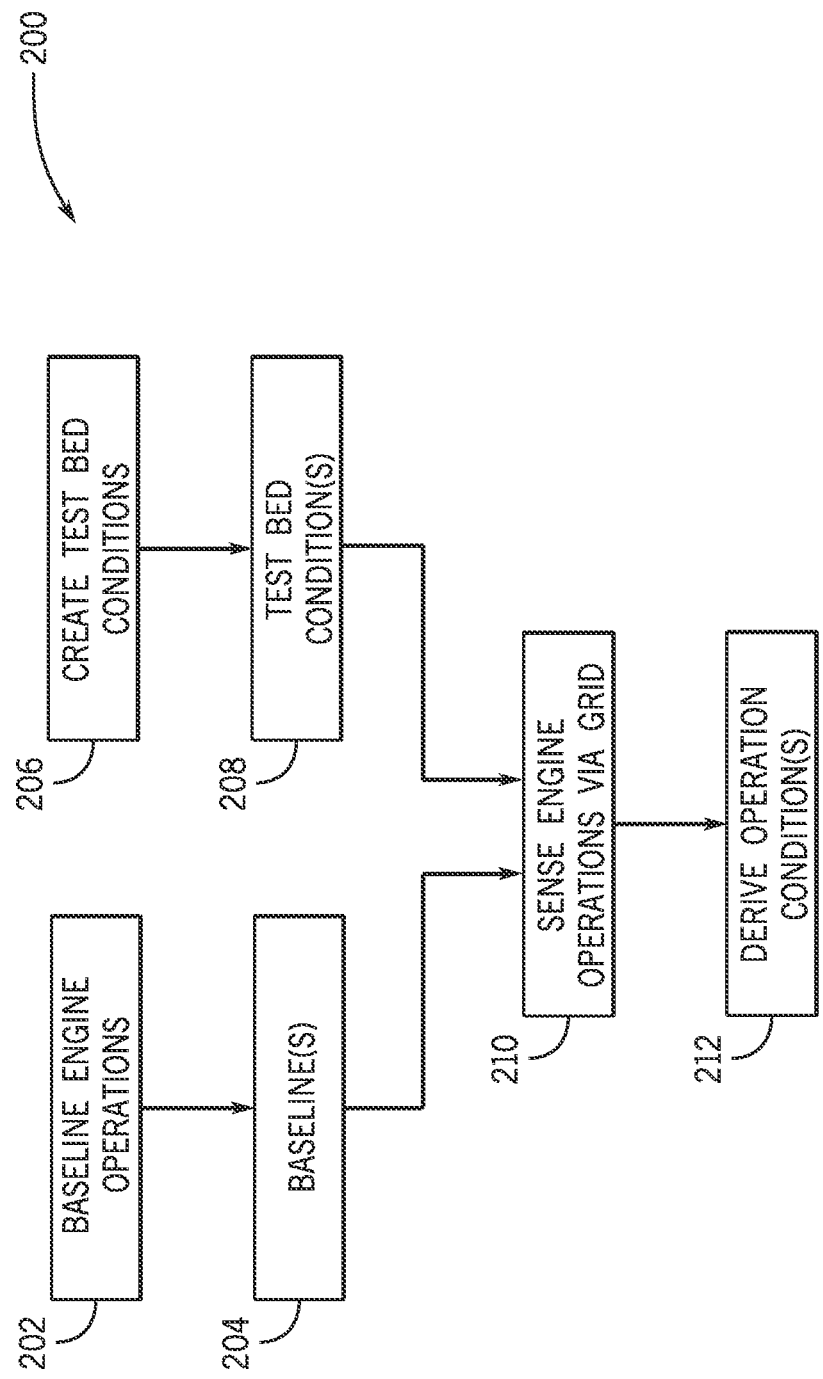

SYSTEMS AND METHODS FOR DETECTION OF ENGINE COMPONENT CONDITIONS VIA EXTERNAL SENSORS

BACKGROUND

The subject matter disclosed herein relates to external sensors, and more specifically, to external sensor systems and method applied to engine component condition detection.

Combustion engines will typically combust a carbonaceous fuel, such as natural gas, gasoline, diesel, and the like, and use the corresponding expansion of high temperature and pressure gases to apply a force to certain components of the engine, e.g., piston disposed in a cylinder, to move the components over a distance. Each cylinder may include one or move valves that open and close correlative with combustion of the carbonaceous fuel. For example, an intake valve may direct an oxidizer such as air into the cylinder, which is then mixed with fuel and combusted. Combustion fluids, e.g., hot gases, may then be directed to exit the cylinder via an exhaust valve. Accordingly, the carbonaceous fuel is transformed into mechanical motion, useful in driving a load. For example, the load may be a generator that produces electric power. It would be beneficial to improve detection of component conditions.

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In a first embodiment, a method is provided. The method includes receiving a plurality of signals representative of an engine noise transmitted via a plurality of noise sensors, wherein the noise sensors are disposed in a grid about an engine. The method further includes receiving a knock sensor signal representative of an engine noise transmitted via a knock sensor. The method additionally includes deriving a combustion event based on the knock sensor signal, and deriving an engine condition based on the plurality of signals and the combustion event. The method also includes communicating the engine condition.

In a second embodiment, a system includes an engine control system comprising a processor configured to receive a plurality of signals representative of an engine noise transmitted via a plurality of noise sensors, wherein the noise sensors are disposed in a grid about an engine. The processor is further configured to receive a knock sensor signal representative of an engine noise transmitted via a knock sensor. The processor is additionally configured to derive a combustion event based on the knock sensor signal, and to derive an engine condition based on the plurality of signals and the combustion event. The process is also configured to communicate the engine condition and to control operations of the engine.

In a third embodiment, a tangible, non-transitory computer readable medium storing code is provided. The code is configured to cause a processor to receive a plurality of signals representative of an engine noise transmitted via a plurality of noise sensors, wherein the noise sensors are disposed in a grid about an engine. The code is additionally configured to cause the processor to receive a knock sensor signal representative of an engine noise transmitted via a knock sensor. The code is further configured to cause the processor to derive a combustion event based on the knock sensor signal, and to derive an engine condition based on the plurality of signals and the combustion event. The code is also configured to cause the processor to communicate the engine condition.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 5 is a flow chart of an embodiment of a process suitable for analyzing a noise data captured by the external grid of sensors shown in FIG. 1.

DETAILED DESCRIPTION

Figure 1:
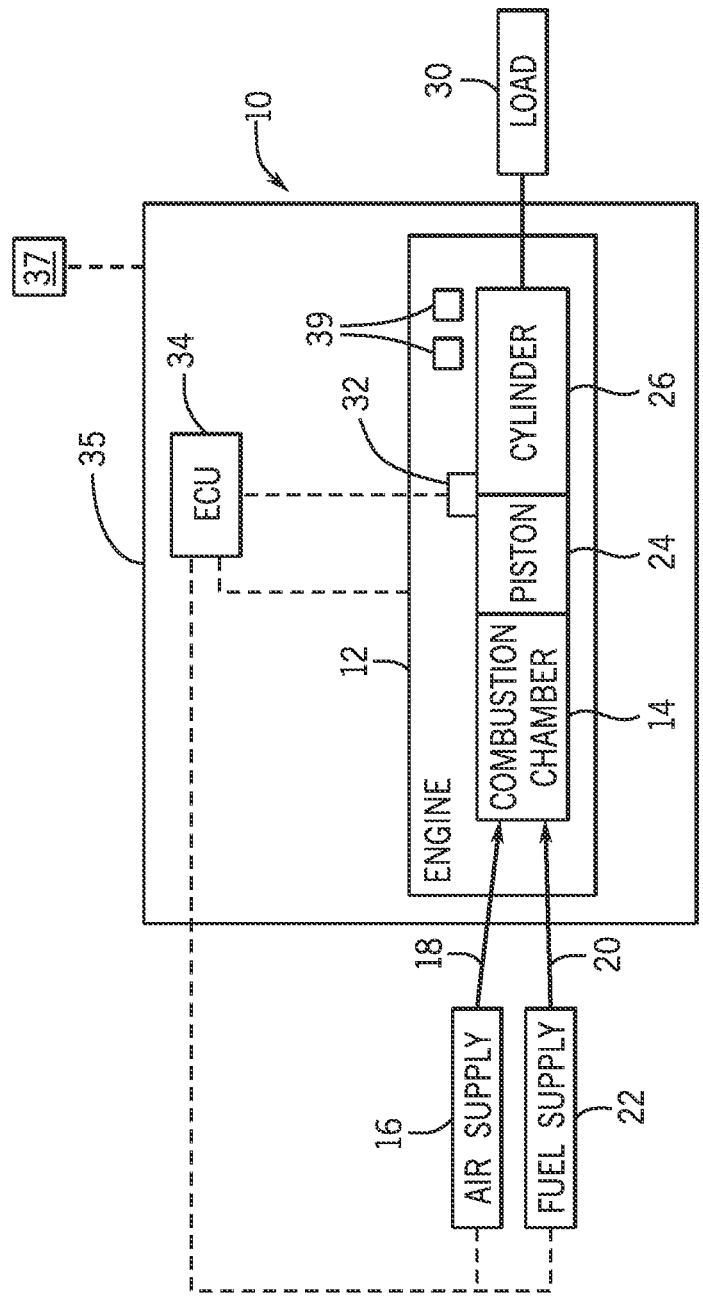
FIG. 1 is a block diagram of an embodiment of an engine driven power generation system and an external grid of sensors, in accordance with aspects of the present disclosure.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

The techniques described herein include systems and methods that use an external grid of a plurality of noise sensors that may detect a dynamic response of a various engine components during engine operations to derive conditions related to the components. Signals from a knock sensor may be used via sequential processing with signals from the external grid to more accurately and efficiently derive a variety of engine conditions. For example, knock sensors signals related to the start of combustion may be detected, and subsequently (e.g., sequentially) grid sensor signals may be processed as described in more detail below to derive a variety of engine conditions related to components such as cylinder head components (e.g., cylinder head and gaskets), cylinder block components (e.g., cylinder block, cylinder sleeves), valves train components (e.g., valves, valve seats, valve stems), camshaft and drive components (e.g., camshaft, cam lobes, timing belts/chains, tensioners), piston components (e.g., pistons, piston rings, connection rods), crankshaft assembly components (e.g., crankshaft, engine bearings, flywheels), gear train components (e.g., gearbox, gears, output shaft), turbocharger components, fuel delivery components, exhaust components, and so on.

Rather than using certain technique such as acoustic beamforming, the techniques described herein may include non-circular external sensor grids, as opposed to circular acoustic beamforming grids. The techniques disclosed herein may additionally or alternatively include grid sensor spacing from noise sources that may be closer or farther away than sensor spacing found in acoustic beamforming. However, sensor spacing from noise sources may be any number of spacings, including spacings used in acoustic beamforming. Further, spacing between sensors may also include any number of distances, as described in more detail below.

The techniques describe herein may additionally include the use of transient states where an engine control system (e.g., engine control unit [ECU]) adjusts certain engine operations, such as revolutions per minute (RPM) ramp rates, engine spark timing, fuel injection sweep rates, engine loads, or a combination thereof, to provide for transient diagnostic states of the engine. During the transient diagnostic states, onboard knock sensors and vibration sensors log data in conjunction with the external sensors disposed on the grid, and/or crankshaft sensors. Spectrum and time-frequency information may then be compared for cross-coherence and may also be compared to a normative baseline (e.g., normal engine operations). Dynamic loading, speed changes, timing sweeps, air/fuel sweeps etc. may advantageously be used to diagnose certain reciprocating engine condition or faults that may not be as easily detected when engine operating conditions are held constant. Some of these conditions may include turbocharger conditions, gear train conditions, valve-train conditions, combustion cylinder balance conditions, induction leaks, exhaust leaks, fuel induction leaks (air/fuel homogeneity conditions), and so on.

Turning now to the drawings, FIG. 1 illustrates a block diagram of an embodiment of a portion of an engine driven power generation system 10. As described in detail below, the system 10 includes an engine 12 (e.g., a reciprocating internal combustion engine) having one or more combustion chambers 14 (e.g., 1, 2, 3, 4, 5, 6, 7, 8, 10, 12, 14, 16, 18, 20, or more combustion chambers 14). Though FIG. 1 shows a combustion engine 12, it should be understood that any reciprocating device may be used. An air supply 16 is configured to provide a pressurized oxidant 18, such as air, oxygen, oxygen-enriched air, oxygen-reduced air, or any combination thereof, to each combustion chamber 14. The combustion chamber 14 is also configured to receive a fuel 20 (e.g., a liquid and/or gaseous fuel) from a fuel supply 22, and a fuel-air mixture ignites and combusts within each combustion chamber 14. The hot pressurized combustion gases cause a piston 24 adjacent to each combustion chamber 14 to move linearly within a cylinder 26 and convert pressure exerted by the gases into a rotating motion, which causes a shaft 28 to rotate. Further, the shaft 28 may be coupled to a load 30, which is powered via rotation of the shaft 28. For example, the load 30 may be any suitable device that may generate power via the rotational output of the system 10, such as an electrical generator. Additionally, although the following discussion refers to air as the oxidant 18, any suitable oxidant may be used with the disclosed embodiments. Similarly, the fuel 20 may be any suitable gaseous fuel, such as natural gas, associated petroleum gas, propane, biogas, sewage gas, landfill gas, coal mine gas, for example.

The system 10 disclosed herein may be adapted for use in stationary applications (e.g., in industrial power generating engines) or in mobile applications (e.g., in cars or aircraft). The engine 12 may be a two-stroke engine, three-stroke engine, four-stroke engine, five-stroke engine, or six-stroke engine. The engine 12 may also include any number of combustion chambers 14, pistons 24, and associated cylinders 26 (e.g., 1-24). For example, in certain embodiments, the system 10 may include a large-scale industrial reciprocating engine 12 having 4, 6, 8, 10, 16, 24 or more pistons 24 reciprocating in cylinders 26. In some such cases, the cylinders 26 and/or the pistons 24 may have a diameter of between approximately 13.5-34 centimeters (cm). In some embodiments, the cylinders 26 and/or the pistons 24 may have a diameter of between approximately 10-40 cm, 15-25 cm, or about 15 cm. The system 10 may generate power ranging from 10 kW to 10 MW. In some embodiments, the engine 12 may operate at less than approximately 1800 revolutions per minute (RPM). In some embodiments, the engine 12 may operate at less than approximately 2000 RPM, 1900 RPM, 1700 RPM, 1600 RPM, 1500 RPM, 1400 RPM, 1300 RPM, 1200 RPM, 1000 RPM, 900 RPM, or 750 RPM. In some embodiments, the engine 12 may operate between approximately 750-2000 RPM, 900-1800 RPM, or 1000-1600 RPM. In some embodiments, the engine 12 may operate at approximately 1800 RPM, 1500 RPM, 1200 RPM, 1000 RPM, or 900 RPM. Exemplary engines 12 may include General Electric Company's Jenbacher Engines (e.g., Jenbacher Type 2, Type 3, Type 4, Type 6 or J920 FleXtra) or Waukesha Engines (e.g., Waukesha VGF, VHP, APG, 275GL), for example.

The driven power generation system 10 may include one or more knock sensors 32 suitable for detecting engine "knock" and/or other run characteristics of the engine 12. The knock sensor 32 may be any sensor configured to sense vibration caused by the engine 12, such as vibration due to detonation, pre-ignition, and or pinging. The knock sensor 32 is shown communicatively coupled to a controller (e.g., a reciprocating device controller), engine control unit (ECU) 34. During operations, signals from the knock sensors 32 are communicated to the ECU 34 to determine if knocking conditions (e.g., pinging), or other behaviors exist. The ECU 34 may then adjust certain engine 12 parameters to ameliorate or avoid the undesirable conditions. For example, the ECU 34 may adjust ignition timing and/or adjust boost pressure to avoid knocking. As further described herein, the knock sensors 32 may additionally detect other vibrations beyond knocking. Although the following techniques for analyzing component health are discussed in terms of a combustion engine, the same techniques may be applied to other reciprocating devices, such as a compressor.

More specifically, an external sensor grid 35 may surround the engine 12 and be communicatively coupled to the ECU 34 and/or an external computing system 37. The external computing system 37 may include a laptop, tablet, cell phone, notebook, server, personal computer, cloud computing system, and so on having a processor suitable for executing computer instructions and a memory suitable for storing the computer instructions. Likewise, the knock sensors 32 may be communicatively coupled to the external computing system 37. In use the ECU 34 and/or external computing system 37 may process data from the knock sensors 32, the external sensor grid 35, and or crank angle sensors (described in more detail below,) to derive a variety of engine 12 conditions.

In one embodiment, the ECU 34 may adjust certain engine operations, such as RPM ramp rates, engine 12 spark timing, fuel injection sweep rates, engine 12 loads, or a combination thereof, to provide for transient diagnostic states of the engine. During the transient diagnostic states, the knock sensors 32 and sensors disposed on the grid 35 may transmit signals to the ECU 34 and/or external computing system 37. The signals may be converted into spectrum and time-frequency information that may then be compared for cross-coherence and may also be compared to a normative baseline (e.g., normal engine 12 operations). In another embodiment, the ECU 34 may not provide for the transient diagnostic states but data from the knock sensors 32 and the grid 35 may still be received and processed by the ECU 34 and/or external computing system 37 to derive a variety of engine conditions via spectrum and time-frequency analysis. Some of these conditions may include turbocharger conditions, gear train conditions, valve-train conditions, combustion cylinder balance conditions, induction leaks, exhaust leaks, fuel induction leaks (air/fuel homogeneity conditions), and so on.

Accordingly, conditions for a variety of engine components 39 may be derived. The engine components 39 may include components such as cylinder head components (e.g., cylinder head and gaskets), cylinder block components (e.g., cylinder block, cylinder sleeves), valves train components (e.g., valves, valve seats, valve stems), camshaft and drive components (e.g., camshaft, cam lobes, timing belts/chains, tensioners), piston components (e.g., pistons, piston rings, connection rods), crankshaft assembly components (e.g., crankshaft, engine bearings, flywheels), gear train components (e.g., gearbox, gears, output shaft), turbocharger components, fuel delivery components, exhaust components, and so on.

Figure 2:
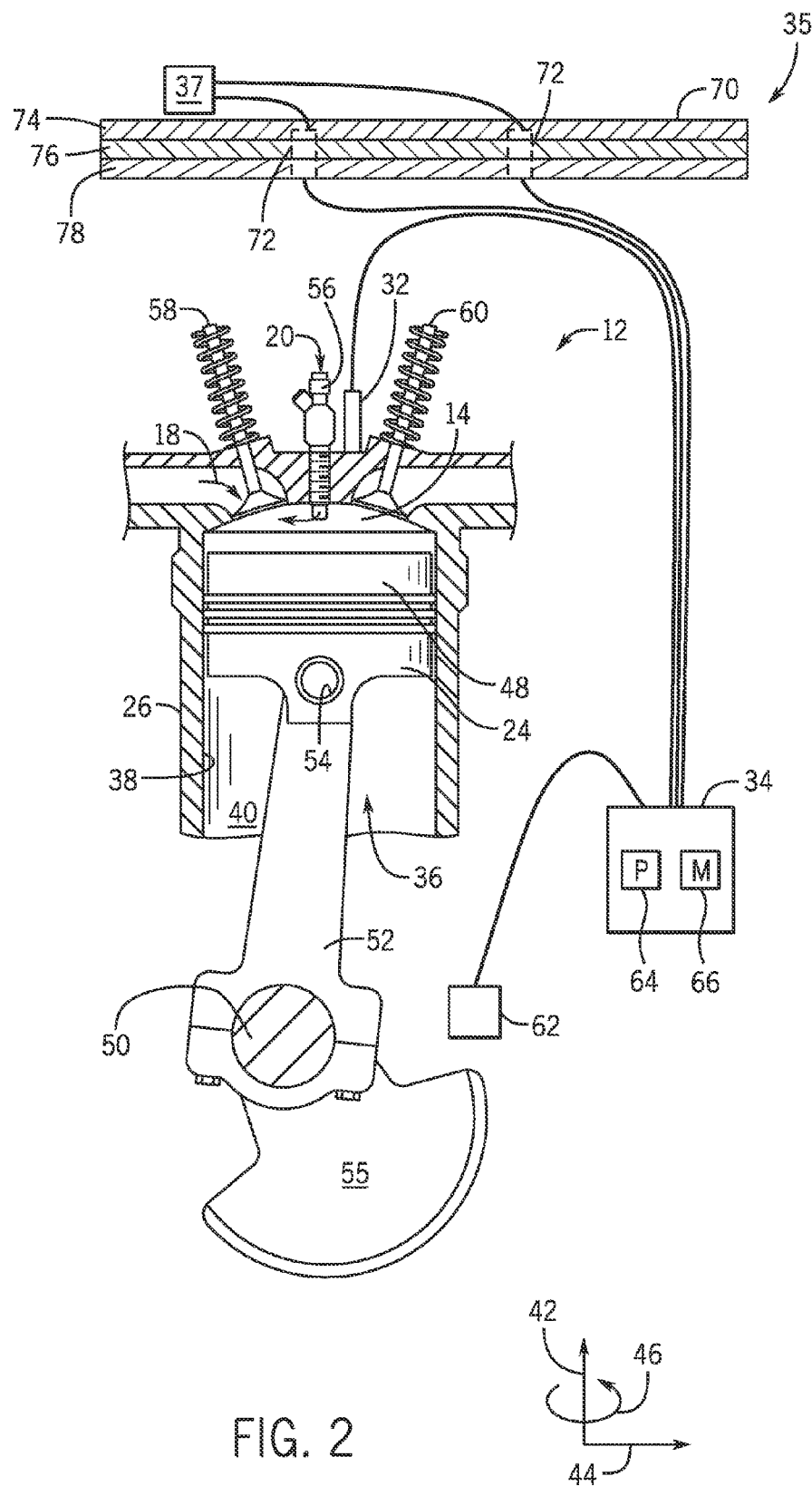
FIG. 2 is a side cross-sectional view of an embodiment of a piston assembly in accordance with aspects of the present disclosure, and a section of the external grid of sensors shown in FIG. 1.

FIG. 2 is a side cross-sectional view of an embodiment of a piston assembly 36 having a piston 24 disposed within a cylinder 26 (e.g., an engine cylinder) of the reciprocating engine 12. The cylinder 26 has an inner annular wall 38 defining a cylindrical cavity 40 (e.g., bore). The piston 24 may be defined by an axial axis or direction 42, a radial axis or direction 44, and a circumferential axis or direction 46. The piston 24 includes a top portion 48 (e.g., a top land). The top portion 48 generally blocks the fuel 20 and the air 18, or a fuel-air mixture, from escaping from the combustion chamber 14 during reciprocating motion of the piston 24.

As shown, the piston 24 is attached to a crankshaft 50 via a connecting rod 52 and a pin 54. Also shown is a counterweight 55 of the crankshaft 50 useful in balancing a weight of a crank throw. The crankshaft 50 translates the reciprocating linear motion of the piston 24 into a rotating motion. As the piston 24 moves, the crankshaft 50 rotates to power the load 30 (shown in FIG. 1), as discussed above. As shown, the combustion chamber 14 is positioned adjacent to the top land 48 of the piston 24. A fuel injector 56 provides the fuel 20 to the combustion chamber 14, and an intake valve 58 controls the delivery of air 18 to the combustion chamber 14. An exhaust valve 60 controls discharge of exhaust from the engine 12. However, it should be understood that any suitable elements and/or techniques for providing fuel 20 and air 18 to the combustion chamber 14 and/or for discharging exhaust may be utilized, and in some embodiments, no fuel injection is used. In operation, combustion of the fuel 20 with the air 18 in the combustion chamber 14 cause the piston 24 to move in a reciprocating manner (e.g., back and forth) in the axial direction 42 within the cavity 40 of the cylinder 26.

During operations, when the piston 24 is at the highest point in the cylinder 26 it is in a position called top dead center (TDC). When the piston 24 is at its lowest point in the cylinder 26, it is in a position called bottom dead center (BDC). As the piston 24 moves from top to bottom or from bottom to top, the crankshaft 50 rotates one half of a revolution. Each movement of the piston 24 from top to bottom or from bottom to top is called a stroke, and engine 12 embodiments may include two-stroke engines, three-stroke engines, four-stroke engines, five-stroke engine, six-stroke engines, or more.

During engine 12 operations, a sequence including an intake process, a compression process, a power process, and an exhaust process typically occurs. The intake process enables a combustible mixture, such as fuel and air, to be pulled into the cylinder 26, thus the intake valve 58 is open and the exhaust valve 60 is closed. The compression process compresses the combustible mixture into a smaller space, so both the intake valve 58 and the exhaust valve 60 are closed. The power process ignites the compressed fuel-air mixture, which may include a spark ignition through a spark plug system, and/or a compression ignition through compression heat. The resulting pressure from combustion then forces the piston 24 to BDC. The exhaust process typically returns the piston 24 to TDC while keeping the exhaust valve 60 open. The exhaust process thus expels the spent fuel-air mixture through the exhaust valve 60. It is to be noted that more than one intake valve 58 and exhaust valve 60 may be used per cylinder 26.

The engine 12 may also include a crankshaft sensor 62, one or more knock sensors 32, and the engine control unit (ECU) 34, which includes a processor 64 and memory 66 (e.g., non-transitory computer readable medium). The crankshaft sensor 62 senses the position and/or rotational speed of the crankshaft 50. Accordingly, a crank angle or crank timing information may be derived. That is, when monitoring combustion engines, timing is frequently expressed in terms of crankshaft 50 angle. For example, a full cycle of a four stroke engine 12 may be measured as a 720° cycle. The one or more knock sensors 32 may be a Piezo-electric accelerometer, a microelectromechanical system (MEMS) sensor, a Hall effect sensor, a magnetostrictive sensor, and/or any other sensor designed to sense vibration, acceleration, sound, and/or movement. In other embodiments, sensor 32 may not be a knock sensor in the traditional sense, but any sensor that may sense vibration, pressure, acceleration, deflection, or movement.

Also shown is a panel or section 70 of the grid 35 having sensors 72. The sensors 72 may be communicatively coupled to the ECU 34 and/or external computing system 37 via wired or wireless conduits. For example, the sensors 72 may be communicatively coupled to the ECU 34 and/or external computing system 37 via on-board diagnostics II (OBD II) conduits, controller area network (CAN) conduits, IEEE 802.11x, WiFi, Bluetooth, wireless mesh conduits, and so on. The sensors 72 may include microphones (acoustic microphones, MEMS microphones), vibration sensors, accelerometers, and the like, suitable for detecting vibrations over a medium such as air.

In the depicted embodiment the panel 70 includes sound deadening or dampening layers 74, 76, and 78. The sound dampening layers 74, 76, and 78 may minimize or eliminate echoes or unwanted noise reflections in embodiments where the engine 12 is disposed inside a container, such as an enclosed trailer, having the grid 35 embedded in the trailer's walls. In this container embodiment, the walls of the container would be manufactured out of panels 70, as shown in more detail below with respect to FIG. 3. The layers 74, 76, and 78 may include wedge foam acoustic layers, fiberglass layers, rockwool layers, porous and non-porous layers noise deadening layers, and more generally, material suitable for soundproofing.

The knock sensor 32 may be capable of detecting engine vibrations and/or certain "signatures" related to a variety of engine conditions even when mounted on the exterior of the cylinder 26. The one or more knock sensors 32 may be disposed at many different locations on the engine 12. For example, in FIG. 2, one knock sensors 32 is shown on the head of the cylinder 26. In other embodiments, one or more knock sensors 32 may be used on the side of the cylinder 26. Additionally, in some embodiments, a single knock sensor 32 may be shared, for example, with one or more adjacent cylinders 26. In other embodiments, each cylinder 26 may include one or more knock sensors 32 on either or both sides of a cylinder 26. The crankshaft sensor 62 and the knock sensor 32 are shown in electronic communication with the engine control unit (ECU) 34. The ECU 34 includes a processor 64 and a memory 66. The memory 66 may store non-transitory code or computer instructions that may be executed by the processor 64. The ECU 34 monitors and controls and operation of the engine 12, for example, by adjusting spark timing, valve 58, 60 timing, adjusting the delivery of fuel and oxidant (e.g., air), and so on.

Knock sensors 32 are used to detect engine knock. Engine knock is the premature combustion of fuel outside the envelope of normal combustion. In some cases, the ECU 34 may attempt to reduce or avoid engine knock when it occurs by adjusting the operating parameters of the engine. For example, the ECU 34 may adjust the air/fuel mix, ignition timing, boost pressure, etc. in an effort to reduce or avoid engine knock. However, knock sensors may also be used to detect other vibrations in an engine unrelated to engine knock.

Figure 3:
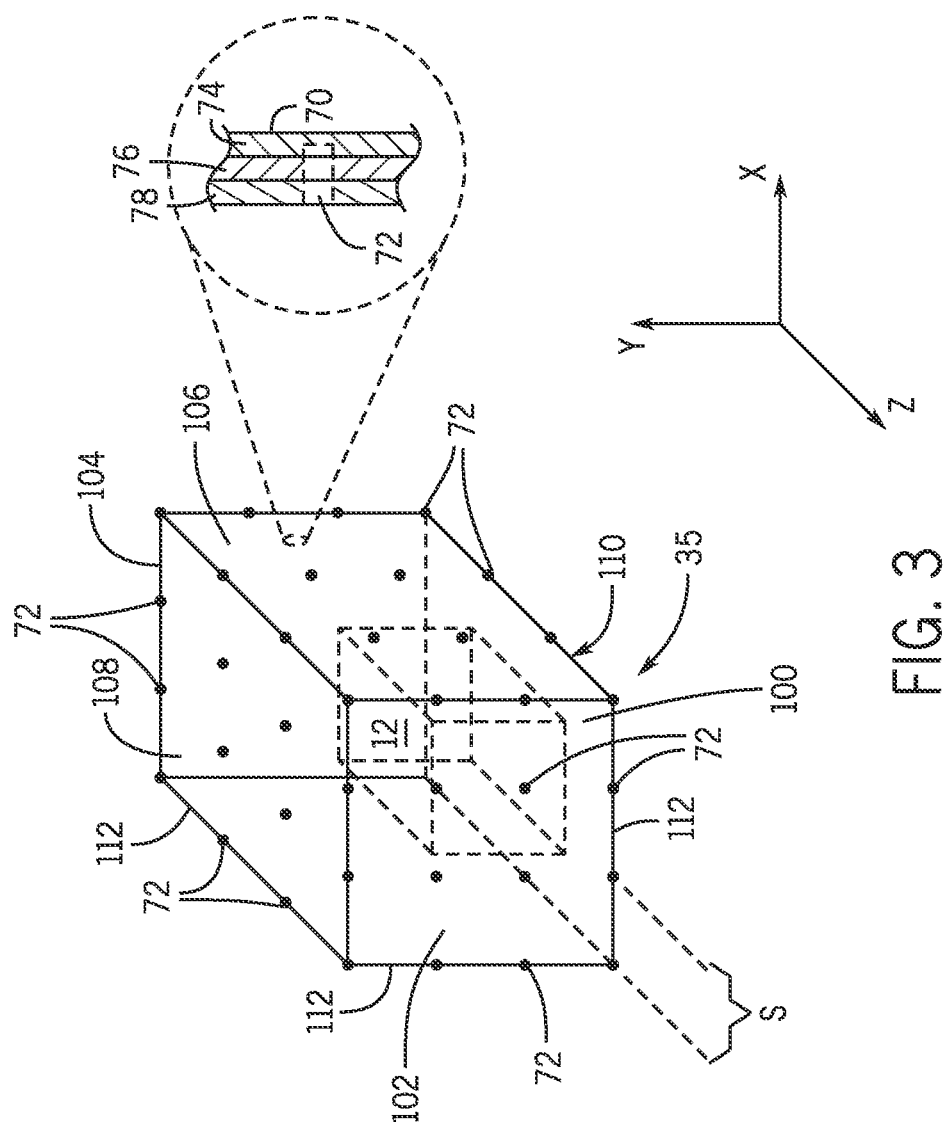
FIG. 3 is a perspective view of the external grid of sensors shown in FIG. 1 surrounding an engine, in accordance with aspects of the present disclosure.

FIG. 3 illustrates an embodiment of the external sensor grid 35 surrounding the engine 12 in three dimensions. In the depicted embodiment, the external sensor grid 35 includes a rectangular shape having six sides 100, 102, 104, 106, 108, and 110. Also depicted is a 3-dimensional (3d) axes 111, showing an x, a y, and a z axis. In one embodiment, the sides 100, 102, 104, 106, 108, and 110 may be manufactured out of the panels 70, as shown. In another embodiment, the panels 70 may not be used an instead, an open rectangular frame manufactured of framing members 112 (e.g., tubular members, square members) may be used. In this open rectangular frame embodiment, the sensors 72 may be supported by wires, other framing members 112, and so on. The open rectangular frame embodiment of having the external sensor grid 35 may advantageously reduce or eliminate noise reflections or echoes by allowing for the noise to traverse through the spacing between framing members 112. In embodiments where a closed environment is desired, the panels 70 may be used to completely or partially enclose the engine 12. Accordingly, the engine 12 may be protected from environmental conditions such as rain, snow, sleet, and the like.

Also depicted is a spacing S between adjacent sensors 72. The spacing S may be between 10 mm to 150 mm, 1 mm to 20 mm, 0.5 mm to 1 m, 0.25 mm to 10 m or more. Certain embodiments may include the same spacing S between adjacent sensors 72. Other embodiments may include different sensor spacing S between sensors 72, for example, sensors 72 closer to the engine 12 may include shorter spacing S while sensors 72 further away from the engine 12 may include longer spacing S. In some embodiments, an equal number of sensors 72 may be disposed in each of the sides 100, 102, 104, 106, 108, and 110. In other embodiments, the number of sensors 72 may vary so that sides 100, 102, 104, 106, 108, and/or 110 may have different numbers of sensors 72. In yet other embodiments certain of the sides 100, 102, 104, 106, 108, and 110 may have less or no sensors 72 when compared to other sides. For example, the side 110 or floor 110 supporting the engine 12 may have very few sensors 72, or no sensors 72.

As depicted, the external sensor grid 35 may completely surround the source of noise, e.g., sources in our about engine 12. Indeed, the external sensor grid 35 may provide for sensors 72 disposed at a variety of planes around the noise source, including planes below (e.g., floor) of the noise source and planes above (e.g., ceiling) of the noise source. Further, in one embodiment, the external sensor grid 35 is advantageously rectangular in shape for easier manufacturing and disposition about the engine 12. In other embodiments, other non-circular shapes may be used, including polyhedron shapes having four or more planar faces (e.g., pyramid, dodecahedron, prisms, icosidodecahedron, and so on).

Figure 4:
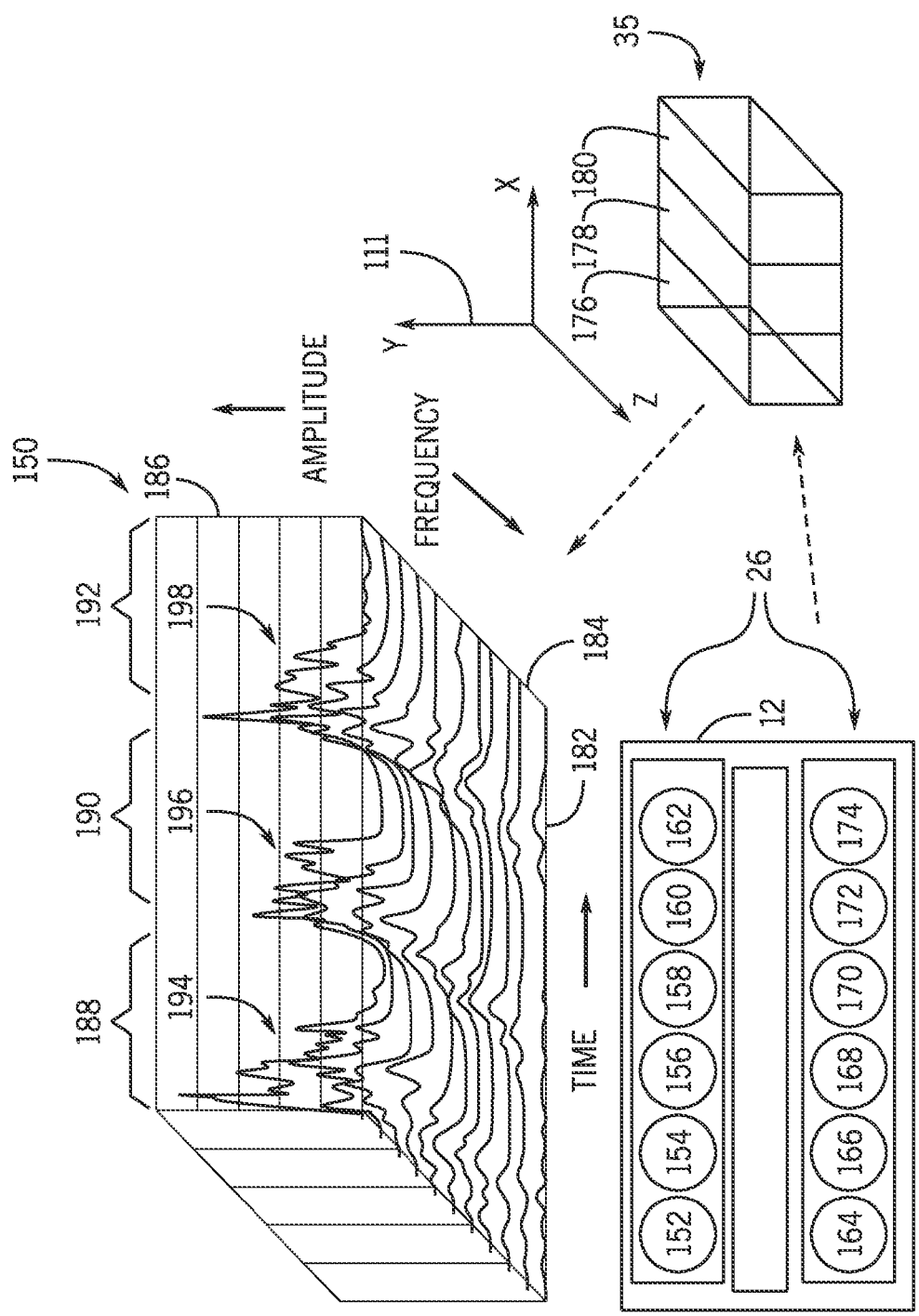
FIG. 4 is an embodiment of a view showing a noise plot captured by the external grid of sensors of FIG. 1 in conjunction with sections or subgrids of the external grid of sensors and a top view of an engine.

In use, the data from the knock sensor 32 and noise sensors 72 may be processed, for example, via 2-dimensional (2D) and/or 3-dimensional (3D) noise spectrum analysis to produce a sample spectrum plot shown in FIG. 4. More specifically, FIG. 4 depicts and embodiment of a 3D noise spectrum plot 150 that may be derived by the external sensor grid 35. Also illustrated is a top block view of the engine 12 having 12 cylinders 26 numbered 152, 154, 156, 158, 160, 162, 164, 166, 168, 170, 172, and 174. Additionally depicted is the external sensor grid 35 with axes 111 as a 3D reference. As the engine 12 operates, one or more of the cylinders 26 may combust fuel and covert combustion into mechanical motion via pistons 24. As illustrated in FIG. 4, a first combustion event for cylinder 152 may first be captured by subgrid or section 176 of the external sensor grid 35 at time T0. As the sound travels through the external sensor grid 35, subgrid or section 178 of the external sensor grid 35 may capture the same first combustion event at time T1, and subgrid or section 180 of the external sensor grid 35 may capture the same first combustion event at time T2. The ECU 34 and/or external computing system 37 may then process the data received at times T0, T1, and T2 to derive the graph 150. For example, the graph 150 may include a time axis 182, a noise frequency axis 184, and a noise amplitude axis 186.

A portion 188 of the graph 150 may correspond to the first combustion event's sounds being recorded by section 176 of the external sensor grid 35. A portion 190 of the graph 150 may correspond to the first combustion event's sounds being recorded by section 178 of the external sensor grid 35. A section 192 of the graph 150 may correspond to the first combustion event's sounds being recorded by section 180 of the external sensor grid 35. Accordingly, 3D spectrum plot 194 is representative of signals processed from section 176 of the external sensor grid 35 at time T0, 3D spectrum plot 196 is representative of signals processed from section 178 of the external sensor grid 35 at time T1, and 3D spectrum plot 198 is representative of signals processed from section 180 of the external sensor grid 35 at time T2.

In another example, if a second combustion event had occurred in cylinder 156, then the section 178 of the external sensor grid 35 may record the second combustion event at time T0. Sections 176 and 180 of the external sensor grid 35 may then both record the second combustion event at time T1 because the sound is likely to propagate from a center of the external sensor grid 35 outwards. By providing for various sections or subgrids of the external sensor grid 35, a more precise and fine-tuned noise analysis may be provided. It is also to be noted that while the external sensor grid 35 is shown as having three portions or subgrids 176, 178, 180, more or less portions or subgrids may be used. For example the external sensor grid 35 may be subdivided into 1, 2, 3, 4, 5, 6, 7, 8, 9, 10 or more subgrids. Indeed, in one embodiment, there may be as many subgrids as the total number of sensors 72 present in the external sensor grid 35, one subgrid per sensor 72.

The captured plots 194, 196, and/or 198 may be analyzed to determine a variety of engine conditions. For example, baseline plots may be derived during normal operations, and the baseline plots may then be compared to the plots 194, 196, and/or 198 to determine if there are variations. For example, statistical techniques such as standard deviation analysis, principal component analysis, multidimensional scaling, data correlation analysis (e.g., Pearson's product-moment coefficient, rank correlation coefficients, and so on) and/or data clustering analysis may be used. Indeed, any number of techniques suitable for comparing one data set to another data set may be used. Variations over a certain amount or percent (e.g., between 0.5%-5%, 0.1%-20%, 0.05-30%) may then be derived and the ECU 34 and/or external computing system 37 may then raise an alarm, an alert, or more generally, notify a user that a condition exists. Other actions may include control actions suitable for controlling the engine 12, for example, by changing spark timing, fuel, turning off engine operations, and so on.

In addition to baselining of normal engine 12 operations, a test bed engine 12 may be used that may enable the creation of a variety of engine 12 conditions. For example, a valve may 58, 60 may be disconnected or valve lash (e.g., distance valve opens) may be varied. Likewise, conditions related to components such as cylinder head components (e.g., cylinder head and gaskets), cylinder block components (e.g., cylinder block, cylinder sleeves), valves train components (e.g., valves, valve seats, valve stems), camshaft and drive components (e.g., camshaft, cam lobes, timing belts/chains, tensioners), piston components (e.g., pistons, piston rings, connection rods), crankshaft assembly components (e.g., crankshaft, engine bearings, flywheels), gear train components (e.g., gearbox, gears, output shaft), turbocharger components, fuel delivery components, exhaust components, and so on may be created on the test bed and condition plots captured based on the created condition(s).

The condition plot(s) may then be compared to plots observed during engine 12 operations, such as plots 194, 196, and/or 198 to determine if certain of the conditions are present. For example, the plots may be compared for similarity, and similar plots (e.g., plots between 100% to 95%, 100% to 80%, 95% to 50%) may be flagged as similar. A number of statistical techniques, such as standard deviation analysis, principal component analysis, multidimensional scaling, data correlation analysis (e.g., Pearson's product-moment coefficient, rank correlation coefficients, and so on) and/or data clustering analysis may be used to determine if the test bed conditions are present. If it is determined that the conditions are present, the ECU 34 and/or external computing system 37 may then raise an alarm, an alert, or more generally, notify a user that a condition exists. Other actions may include control actions suitable for controlling the engine 12, for example, by changing spark timing, fuel, turning off engine operations, and so on. It is also to be noted that the baseline analysis and test bed condition analysis may be combined to determine if engine 12 conditions are present during engine 12 operations.

It is to be noted that the analysis of the data supplied via the external sensor grid 35 may incorporate data from the knock sensor 32 and/or crankshaft sensor 62. For example, the knock sensor 32 may supply data useful in deriving which one of the cylinders 26 (e.g., cylinders 152-174) is firing, and the crankshaft sensor 62 may provide for engine timing information, such as crank angle information. Accordingly, a process may first use the knock sensor 32 and/or crankshaft sensor 62 to derive which of the cylinders 26 is firing as well as the timing information (e.g., crank angle information). Data (e.g., plots 194, 196, 198) from the external sensor grid 35 may then be further analyzed with a priori knowledge that certain of the cylinders 26 is or has fired and/or engine 12 timing information. In one embodiment, the knock sensor 32 and/or crankshaft sensor 62 data may be processed first to determine the cylinder 26 that is firing and/or the engine 12 timing information, and then data from the external sensor grid 35 may be processed second to determine engine 12 conditions. The baselining of normal engine 12 operations (e.g., normative baselining) and/or the test bed conditions may incorporate the knock sensor 32 data and/or the crankshaft sensor 62 data to further improve the detection of engine 12 conditions.

FIG. 5 is a flow chart depicting a process 200 suitable for analyzing engine 12 data via the knock sensors 32 and/or the external computing system 37. The process 200 may be implemented as computer code or instructions executable via the processor 64 and stored in the memory 66 and/or the external computing system 37. In the depicted embodiment, the process 200 may baseline (block 202) normal engine operations to create one or more baselines 204. As mentioned above, the baselines 204 may be created by recording engine operations via the knock sensor 32, the crankshaft sensor 62, and or sensors 72 disposed in the external sensor grid 35. 3D spectrums similar those in FIG. 4 (e.g., 194, 196, 198) may be created and saved as the baseline(s) 204. The process 200 may additionally or alternatively create (block 206) a variety of engine 12 conditions in a test bed, and then provide recordings of the test bed conditions 208 The conditions 208 may also include 3D spectrums similar those in FIG. 4 (e.g., 194, 196, 198). The conditions 208 may be compared to current engine operation conditions (e.g., condition-based analysis) to determine if the engine 12 is currently experiencing one or more of the conditions 208.

The process 200 may then sense (block 210) engine 12 operations by using the external sensor grid 35, the knock sensors 32, and/or the external computing system 37. In some embodiments, the sensing (block 210) may include sensing operations with the use of transient states where the engine control system (e.g., engine control unit [ECU] 34, external computing system 37) adjusts certain engine 12 operations, such as revolutions per minute (RPM) ramp rates, engine spark timing, fuel injection sweep rates, engine loads, or a combination thereof, to provide for transient diagnostic states of the engine while sensing the operations (block 210).

The baseline(s) 204 and/or test bed condition(s) 208 may be used to compare current engine 12 operations to determine deviations from normal operations and/or the existence of certain of the condition(s) 28. By comparing current engine 12 operations to the baseline(s) 204 and/or test bed condition(s) 208, the process 200 may derive (block 212) certain of the engine 12 operation conditions, such as conditions related to components such as cylinder head components (e.g., cylinder head and gaskets), cylinder block components (e.g., cylinder block, cylinder sleeves), valves train components (e.g., valves, valve seats, valve stems), camshaft and drive components (e.g., camshaft, cam lobes, timing belts/chains, tensioners), piston components (e.g., pistons, piston rings, connection rods), crankshaft assembly components (e.g., crankshaft, engine bearings, flywheels), gear train components (e.g., gearbox, gears, output shaft), turbocharger components, fuel delivery components, exhaust components, and so on. The process 200 may then communicate (block 214) the derived engine 12 conditions. For example, the process 200 may display the one or more engine 12 conditions in a display communicatively coupled to the ECU 34, set an error code (e.g., controller area network [CAN] code, on-board diagnostics II [OBD-II] code), set an alarm or an alert, and so on. By applying sensors 72 diposed in external sensor grid 35, with additional sensors such as the knock sensors 32 and/or crankshaft sensors 62, the techniques described herein may enhance engine 12 operations and maintenance processes.

Technical effects of the invention include detecting engine vibrations via certain sensors, sensors disposed in an external sensor grid surrounding the engine. Signals from a knock sensor may be used via sequential processing with signals from the external grid to more accurately and efficiently derive a variety of engine conditions. Transient states where an engine control system adjusts certain engine operations, such as RPM ramp rates, engine spark timing, fuel injection sweep rates, engine loads, or a combination thereof, to provide for transient diagnostic states of the engine. During the transient diagnostic states, onboard knock sensors and vibration sensors log data in conjunction with the external sensors disposed on the grid, and or crankshaft sensors. Spectrum and time-frequency information may then be compared for cross-coherence and may also be compared to a normative baseline (e.g., normal engine operations).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method, comprising:
receiving a plurality of signals representative of an engine noise transmitted via a plurality of noise sensors, wherein the noise sensors are disposed in a grid about an engine;
receiving a knock sensor signal representative of an engine noise transmitted via a knock sensor;
deriving a combustion event based on the knock sensor signal;
deriving an engine condition based on the plurality of signals and the combustion event; and
communicating the engine condition.

2. The method of claim 1, wherein deriving the engine condition based on the on the plurality of signals and the combustion event comprises a sequential processing of data so the knock sensor signal is processed at a first time and the plurality of signals is processed at a second time after the first time.

3. The method of claim 1, comprising receiving a crank angle signal representative of a position of a crankshaft, and wherein deriving the engine condition comprises deriving the engine condition based on the plurality of signals, the combustion event, and the position of the crankshaft.

4. The method of claim 1, wherein the grid comprises a non-circular grid.

5. The method of claim 1, wherein deriving the engine condition based on the plurality of signals comprises applying a 3-dimensional (3D) spectrographic analysis to the plurality of signals.

6. The method of claim 5, wherein applying the 3D spectrographic analysis comprises dividing data from received from the plurality of noise sensors into a plurality of subgrid data sections via a time dimension.

7. The method of claim 6, wherein each of the subgrid data sections comprises a noise corresponding to a cylinder combustion event received at increasing times.

8. The method of claim 1, wherein deriving the engine condition comprises applying a normative baselining analysis to the plurality of signals, applying a condition-based analysis to the plurality of signals, or a combination thereof.

9. The method of claim 1, wherein deriving the engine condition comprises operating the engine at a transient state and observing transient state operations via the plurality of noise sensors.

10. A system, comprising:
an engine control system comprising a processor configured to:
receive a plurality of signals representative of an engine noise transmitted via a plurality of noise sensors, wherein the noise sensors are disposed in a grid about an engine;
receive a knock sensor signal representative of an engine noise transmitted via a knock sensor;
derive a combustion event based on the knock sensor signal;
derive an engine condition based on the plurality of signals and the combustion event;
communicate the engine condition; and
control operations of the engine.

11. The system of claim 10, wherein the processor is configured to control operations of the engine at a transient state to provide for transient state data to the plurality of noise sensors.

12. The system of claim 11, wherein the transient state comprises applying an RPM ramp rate, an engine spark timing change, a fuel injection sweep rate, an engine load change, or a combination thereof.

13. The system of claim 10, correlating the engine condition to the signal comprises verifying that the component was at a second position during engine operations by querying the lookup table.

14. The system of claim 10, wherein the processor is configured to receive a crank angle signal representative of a position of a crankshaft, and wherein deriving the engine condition comprises deriving the engine condition based on the plurality of signals, the combustion event, and the position of the crankshaft.

15. The system of claim 10, wherein the processor is configured to derive the engine condition based on the plurality of signals by applying a 3-dimensional (3D) spectrographic analysis to the plurality of signals.

16. The system of claim 10, comprising the grid, wherein the grid comprises a non-circular grid.

17. A tangible, non-transitory computer readable medium storing code configured to cause a processor to:
  receive a plurality of signals representative of an engine noise transmitted via a plurality of noise sensors, wherein the noise sensors are disposed in a grid about an engine;
  receive a knock sensor signal representative of an engine noise transmitted via a knock sensor;
  derive a combustion event based on the knock sensor signal;
  derive an engine condition based on the plurality of signals and the combustion event;
  communicate the engine condition.

18. The tangible, non-transitory computer readable medium of claim 17, wherein the code configured to cause the processor to derive the engine condition based on the plurality of signals and the combustion event comprise code configured to cause the processor to sequentially process data so the knock sensor signal is processed at a first time and the plurality of signals is processed at a second time after the first time.

19. The tangible, non-transitory computer readable medium of claim 17, wherein the code is configured to cause the processor to receive a crank angle signal representative of a position of a crankshaft, and wherein deriving the engine condition comprises deriving the engine condition based on the plurality of signals, the combustion event, and the position of the crankshaft.

20. The tangible, non-transitory computer readable medium of claim 17, wherein the code configured to cause the processor to derive the engine condition comprises code configured to cause the processor to apply a normative baselining analysis to the plurality of signals, apply a condition-based analysis to the plurality of signals, or a combination thereof.

* * * * *